US00PP34174P2

(12) United States Plant Patent
de Vries

(10) Patent No.: US PP34,174 P2
(45) Date of Patent: Apr. 26, 2022

(54) ***EPIPHYLLUM* PLANT NAMED 'FIRE'**

(50) Latin Name: *Epiphyllum anguligerum*
Varietal Denomination: FIRE

(71) Applicant: Menno de Vries, Nieuwveen (NL)

(72) Inventor: Menno de Vries, Nieuwveen (NL)

(73) Assignee: De Vries Succulenten B.V.

( * ) Notice: Subject to any disclaimer, the term of this patent is extended or adjusted under 35 U.S.C. 154(b) by 0 days.

(21) Appl. No.: 17/223,870

(22) Filed: Apr. 6, 2021

(51) Int. Cl.
*A01H 5/02* (2018.01)
*A01H 6/24* (2018.01)

(52) U.S. Cl.
USPC ..... Plt./372
CPC ..... *A01H 6/24* (2018.05)

(58) Field of Classification Search
USPC ..... Plt./372, 263.1
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Epiphyllum* plant named 'FIRE' is disclosed, characterized by distinctively red new phylloclades, turning bright green with maturity. The new variety is an *Epiphyllum*, typically produced as an indoor or outdoor ornamental plant.

1 Drawing Sheet

Latin name of the genus and species: *Epiphyllum anguligerum.*

Variety denomination: 'FIRE'.

BACKGROUND OF THE INVENTION

The new cultivar is a product of chance discovery. The parent is an unpatented, unnamed A *Epiphyllum anguligerum*. 'FIRE' was discovered as a naturally occurring leaf mutation by the inventor in 2017 in De Vries, The Netherlands at a commercial nursery.

Asexual reproduction of the new cultivar 'FIRE' was first performed in De Vries, The Netherlands, at a commercial laboratory by leaf cuttings in August of 2017. 'FIRE' has since produced several generations and has shown that the unique features of this cultivar are stable and reproduced true to type.

SUMMARY OF THE INVENTION

The cultivar 'FIRE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FIRE'. These characteristics in combination distinguish 'FIRE' as a new and distinct *Epiphyllum* cultivar:

1. Red young phylloclade color.
2. Distinct narrow young phylloclade.
3. Bright green mature phylloclade.

PARENTAL COMPARISON

Plants of the new cultivar 'FIRE' are similar to the parent in most horticultural characteristics. However, plants of the new variety differ from the seed parent in the following:

1. New cultivar produces red new phylloclades, new phylloclades of the parent are green.

COMMERCIAL COMPARISON

'FIRE' can be compared to an unnamed, unpatented variety of *Epiphyllum oxypetalum* found in commercial nurseries. The new variety has some horticultural similarities to *Epiphyllum oxypetalum*, however, the new variety differs in the following:

1. The new cultivar produces red new phylloclades; young phylloclades of this comparator are green.
2. Plants of the new variety form phylloclades which do not grow more than approximately 40 cm; phylloclades of this comparator can grow up to 6 meters.
3. Phylloclade margins of the new variety are less crenate and undulate than phylloclade margins of this comparator.

'FIRE' can also be compared to an unnamed, unpatented variety of *Epiphyllum pumilum* found in commercial nurseries. The new variety has some horticultural similarities to *Epiphyllum pumilum*, however, the new variety differs in the following:

1. The new cultivar produces red new phylloclades; young phylloclades of this comparator are green.
2. Plants of the new variety form phylloclades which do not grow more than approximately 40 cm; phylloclades of this comparator can grow up to 5 meters.
3. Phylloclade margins of the new variety are less undulate than phylloclade margins of this comparator.
4. Phylloclade margins of the new variety are shallowly crenate, phylloclade margins of this comparator are toothed.

BRIEF DESCRIPTION OF THE PHOTOGRAPH

The accompanying photograph illustrates in full color a typical plant of 'FIRE' grown in a greenhouse in De Vries, The Netherlands. This plant is approximately 7 months old from a rooted leaf cutting, shown in a 14 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 edition, except where general terms of ordinary dictionary significance are used. The following observations and measurements describe 'FIRE' plants in a commercial greenhouse in Nieuwveen, The Netherlands during February. Temperatures ranged from 18° C. to 35° C. during the day, and 18° C. to 22° C. during the night. No artificial light, photoperiodic treatments or chemical treatments were given to the plants. Measurements and numerical values represent averages of typical plant types.

Botanical classification: *Epiphyllum* hybrid 'FIRE'.

Age of the plant described: 7 months in a 14 cm pot.

PROPAGATION

Time to initiate roots: Approximately 7 days at 22° C.

Time to produce a rooted liner: About 42 days at 22° C.

Propagation method: Leaf cutting.

PLANT

Growth habit: Broad obovate phylloclades arching and weeping.

Container size: 14 cm.

Height: 58.2 cm to top of foliar plane.

Plant spread: Average 33.3 cm.

Growth rate: Moderate to rapid.

Branching characteristics: Main phylloclades grow from the base, with lateral phylloclades emerging from the mains.

Phylloclades: On average 11 main phylloclades and 55 lateral phylloclades.

*Length*.—Average 30.3 cm.

*Width*.—flattened and slightly succulent, average diameter at widest point 2.8 cm, average diameter at narrowest, 0.3 cm.

*Internode*.—Leaf spines occur in clusters, average internode length between clusters 2.6 cm.

*Shape*.—Linear. Flattened.

*Margin*.—Broadly crenate.

*Aspect*.—Moderately undulate, weeping.

*Apex*.—Irregular broad acute.

*Base*.—Truncate.

*Appearance*.—Glossy all surfaces.

*Angle from center*.—Average angle 20°, range between 0° and 45°.

*Strength*.—Sturdy and strong.

*Texture*.—Glabrous.

*Color*.—Immature, both sides: Near RHS Greyed-Orange 173A towards apex, turning 174A slightly lower. When beginning to mature changes to Yellow-Green 152A. Mature, upper surface: Near RHS Green 137A, main vein colored Green 143B. Mature, lower surface: Near RHS Yellow-Green 146A mixed with Green N137B. Main vein colored Yellow-Green 147B. Color at internodes: Both sides near RHS Green N137B.

Root description: Moderately dense, fibrous. White, around RHS 155A. No additional root structures.

FOLIAGE

Leaf: Foliage consists of leaf spines, as typical for *Epiphyllum*.

*Leaf spines*.—

*Arrangement*.—Single, arranged in clusters of up to 15 leaf spines per cluster in young phylloclades, leaf spines dropped in older phylloclades.

*Average length*.—0.7 cm. Range between 0.3 to 1.1 cm.

*Average width*.—1 mm.

*Shape*.—Filiform.

*Apex*.—Pointed, not sharp.

*Base*.—Truncate.

*Margin*.—Entire.

*Aspect*.—Straight.

*Texture of upper surface*.—Glabrous.

*Texture of under surface*.—Glabrous.

*Appearance upper surface*.—Matte.

*Appearance under surface*.—Matte.

*Color*.—Young foliage upper side: Near RHS Greyed-White 156D. Young foliage under side: Near RHS Greyed-White 156D. Mature foliage upper side: Near RHS Greyed-White 156D. Mature foliage under side: Near RHS Greyed-White 156D.

Venation: No visible venation.

FLOWER

Flowering: Not observed.

OTHER CHARACTERISTICS

Seeds and fruits: None observed to date.

Temperature tolerance: Tolerates temperatures up to at least 40 degrees C. and at least as low as 4° C.

Drought tolerance: Not observed, expected similar drought tolerance as typical to species.

Disease/pest resistance: Neither resistance nor susceptibility to normal diseases and pests known to *Epiphyllum* observed to date.

What is claimed is:

1. A new and distinct cultivar of *Epiphyllum* plant named 'FIRE' as herein illustrated and described.

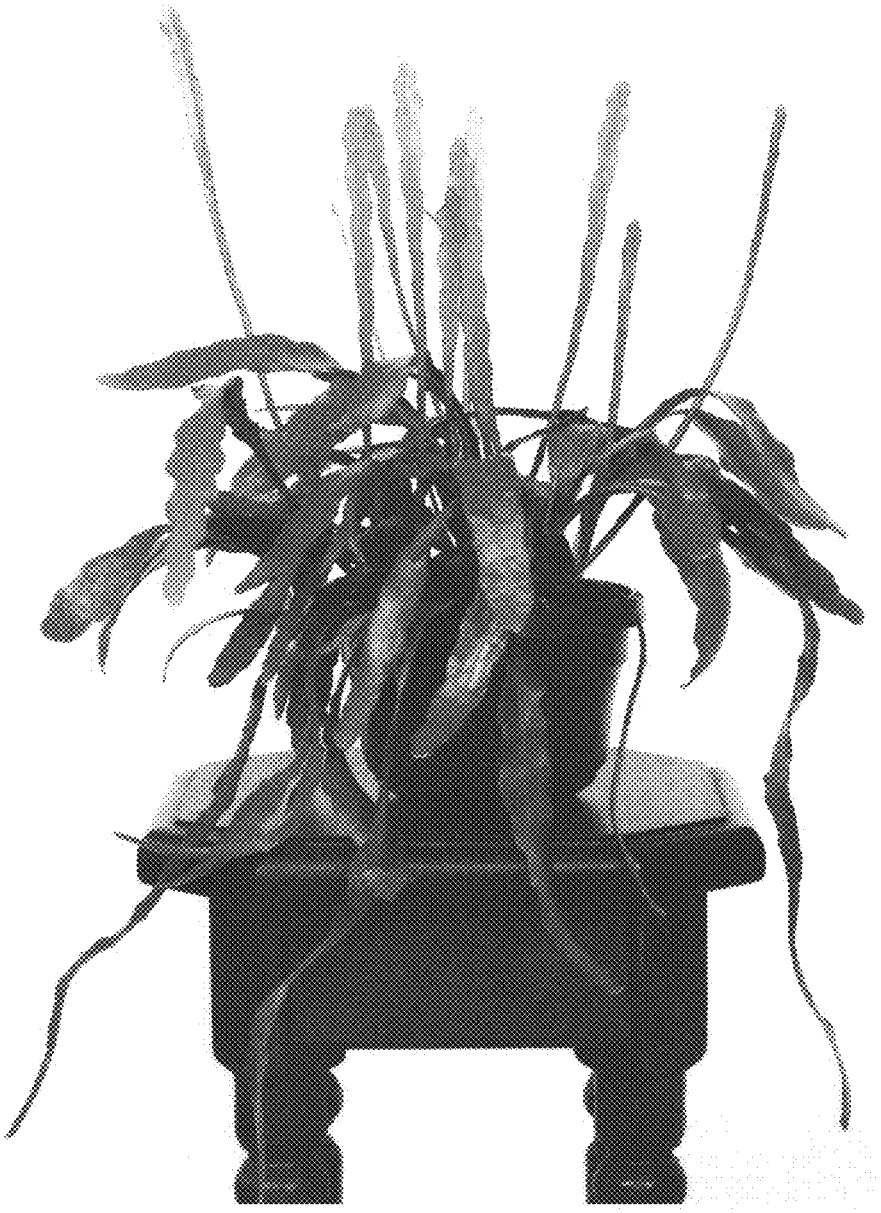

* * * * *